United States Patent [19]

Claremon et al.

[11] Patent Number: 5,726,171
[45] Date of Patent: Mar. 10, 1998

[54] N-(1-ALKYL-5-PHENYL-2,3,4,5-TETRAHYDRO-1H-BENZO[B][1,4]DIAZEPIN-3YL)-ACETAMIDES

[76] Inventors: David A. Claremon; Nigel Liverton; Garry R. Smith; Harold G. Selnick, all of c/o Merck & Co., Inc. Sumneytown Pike, West Point, Pa. 19486

[21] Appl. No.: 616,239

[22] Filed: Mar. 13, 1996

Related U.S. Application Data

[63] Continuation of Ser. No. 476,534, Jun. 7, 1995.
[51] Int. Cl.⁶ .......................... A61K 31/55; C07D 243/12
[52] U.S. Cl. .................................. 514/221; 540/517
[58] Field of Search ........................ 514/221; 540/517

[56] References Cited

U.S. PATENT DOCUMENTS

| | | | |
|---|---|---|---|
| 4,470,988 | 9/1984 | Watthey | 424/263 |
| 4,473,575 | 9/1984 | Watthey | 424/263 |
| 4,503,060 | 3/1985 | Walther et al. | 514/214 |
| 4,507,313 | 3/1985 | Braestrap et al. | 514/220 |
| 4,537,885 | 8/1985 | Watthey | 514/183 |
| 4,600,534 | 7/1986 | Bach et al. | 260/239.3 |
| 4,692,522 | 9/1987 | Parsons et al. | 540/523 |
| 4,775,671 | 10/1988 | Hunkeler et al. | 514/220 |
| 4,820,834 | 4/1989 | Evans et al. | 540/504 |
| 4,847,248 | 7/1989 | Freidinger et al. | 514/214 |
| 4,992,437 | 2/1991 | Naka et al. | 514/220 |
| 5,004,741 | 4/1991 | Evans et al. | 514/221 |
| 5,008,263 | 4/1991 | Cooper et al. | 540/517 |
| 5,055,464 | 10/1991 | Murakami et al. | 514/211 |
| 5,166,151 | 11/1992 | Freidinger et al. | 514/215 |
| 5,206,234 | 4/1993 | Bock et al. | 514/213 |
| 5,220,018 | 6/1993 | Bock et al. | 540/509 |
| 5,302,591 | 4/1994 | Fletcher et al. | 514/221 |
| 5,324,726 | 6/1994 | Bock et al. | 514/221 |
| 5,338,861 | 8/1994 | Botta et al. | 548/552 |
| 5,360,802 | 11/1994 | Chambers et al. | 514/221 |
| 5,410,049 | 4/1995 | Chambers | 540/504 |
| 5,426,185 | 6/1995 | Baldwin et al. | 540/509 |
| 5,428,157 | 6/1995 | Baldwin et al. | 540/509 |
| 5,438,055 | 8/1995 | Baldwin et al. | 514/221 |
| 5,439,905 | 8/1995 | Naka et al. | 514/220 |
| 5,439,906 | 8/1995 | Bock et al. | 514/220 |
| 5,504,077 | 4/1996 | Collins et al. | 514/211 |

FOREIGN PATENT DOCUMENTS

| | | |
|---|---|---|
| 1 190 708 | 7/1985 | Canada . |
| 0 107 095 A1 | 5/1984 | European Pat. Off. . |
| 0 514 133 A1 | 11/1992 | European Pat. Off. . |
| 0 538 945 A1 | 4/1993 | European Pat. Off. . |
| 0 566 175 A2 | 10/1993 | European Pat. Off. . |
| WO 94/05673 | 3/1974 | WIPO . |
| WO 93/02078 | 2/1993 | WIPO . |
| WO 93/07131 | 4/1993 | WIPO . |
| WO 93/08176 | 4/1993 | WIPO . |
| WO 93/15068 | 8/1993 | WIPO . |
| WO 93/17011 | 9/1993 | WIPO . |
| WO 93/19063 | 9/1993 | WIPO . |

OTHER PUBLICATIONS

J. Gen. Physiol., vol. 96, pp. 195–215 (Jul. 1990), by M.C. Sanguinetti, et al.
J. Cardiovasc. Pharmacol., vol. 20, (Suppl. 2) pp. S17–S22 (1992), by L.M. Hondeghem.

*Primary Examiner*—Mukund J. Shah
*Assistant Examiner*—Bruck Kifle
*Attorney, Agent, or Firm*—Valerie J. Camara; Mark R. Daniel

[57] ABSTRACT

This invention is concerned with novel compounds represented by structural formula I

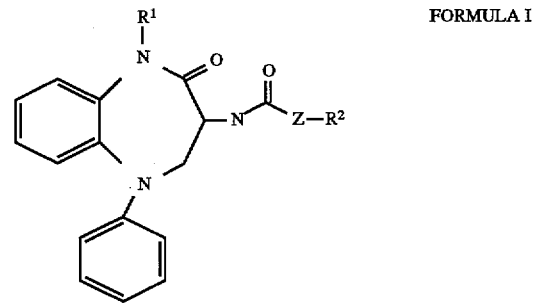

FORMULA I which are useful in the treatment of arrhythmia.

18 Claims, No Drawings

N-(1-ALKYL-5-PHENYL-2,3,4,5-TETRAHYDRO-1H-BENZO[B][1,4]DIAZEPIN-3YL)-ACETAMIDES

This is a continuation of application Ser. No. 08/476,534 filed on Jun. 7, 1995.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, agents which exhibit both satisfactory effects and high safety profiles have not been marketed. For example, antiarrythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrhythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drags which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formula I

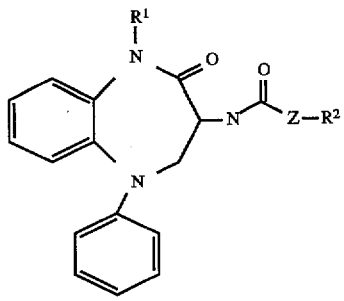

FORMULA I where
$R^1$ is $C_{1-6}$ alkyl, either straight or branch chain; substituted $C_{1-6}$alkyl, either straight or branch chain wherein the substitutents are selected from F, $C_{3-8}$ cycloalkane, —OH, —$CF_3$, and Z is
1) $C_{1-6}$ alkyl, either straight or branch chain,
2) substituted $C_{1-6}$ alkyl, either straight or branch chain, wherein the substitutents are selected from F, OH, $NO_2$,
2) $C_{2-4}$ alkenylene, either straight or branch chain,
3) —$(CH_2)_m$—W—$(CH_2)_n$— wherein m and n are independently 0, 1, 2, 3 or 4 and W is —O—, —S— or —NH,
4) $C_{3-6}$ cycloalkane,
5) $C_{3-6}$ cycloalkylene, or
6) single bond;
$R^2$ is
1) phenyl, either unsubstituted or substituted with one or two substituents selected from
a) —$NO_2$,
b) —Cl, Br, F, or I,
c) —$CF_3$,
d) —$C_{1-3}$ alkyl,
e) —$C_{1-3}$ alkoxy,
f) —CN,
g) -methylenedioxy,
2) $C_{5-7}$ cycloalkyl, either unsubstituted or substituted with one or two substitutents selected from
a) —$NO_2$, —OH,
b) F,
c) —$CF_3$,
d) —$C_{1-3}$ alkyl,
e) —$C_{1-3}$ alkoxy,
f) —CN,
g) -methylenedioxy,
or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment.

DETAILED DESCRIPTION OF THE INVENTION

The novel compounds of this invention have structural formulae

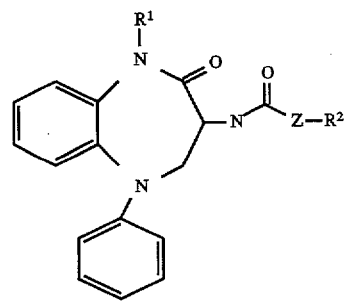

FORMULA I where
$R^1$ is $C_{1-6}$ alkyl, either straight or branch chain; substituted $C_{1-6}$alkyl, either straight or branch chain wherein the substitutents are selected from F, $C_{3-8}$ cycloalkane, —OH, —$CF_3$, and Z is
1) $C_{1-6}$ alkyl, either straight or branch chain, 2) substituted $C_{1-6}$ alkyl, either straight or branch chain, wherein the substitutents are selected from F, OH, $NO_2$, 2) $C_{2-4}$ alkenylene, either straight or branch chain, 3) —$(CH_2)_m$—W—$(CH_2)_n$— wherein m and n are independently 0, 1, 2, 3 or 4 and W is —O—, —S—or —NH, 4) $C_{3-6}$ cycloalkane, 5) $C_{3-6}$ cycloalkylene, or 6) single bond;

$R^2$ is 1) phenyl, either unsubstituted or substituted with one or two substituents selected from a) —$NO_2$, OH, b) —Cl, Br, F, or I, c) —$CF_3$, d) —$C_{1-3}$ alkyl, e) —$C_{1-3}$ alkoxy, f) —CN, g) -methylenedioxy, 2) $C_{5-7}$ cycloalkyl, either unsubstituted or substituted with one or two substituents selected from a) —$NO_2$, b) —F, c) —$CF_3$, d) —$C_{1-3}$ alkyl, e) —$C_{1-3}$ alkoxy, f) —CN, g) -methylenedioxy, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment. These compounds include pharmaceutically acceptable crystal forms and hydrates of the compounds of Formula I, which are antiarrhythmic agents.

Examples of some of the compounds which form the embodiment of this invention are N-(4-Oxo-1-phenyl-5-(2-propyl)-2,3,4,5-tetrahydro-1H-1,5-benzodiazepin-3-yl)-3-(2,4-dichlorophenyl) propionamide

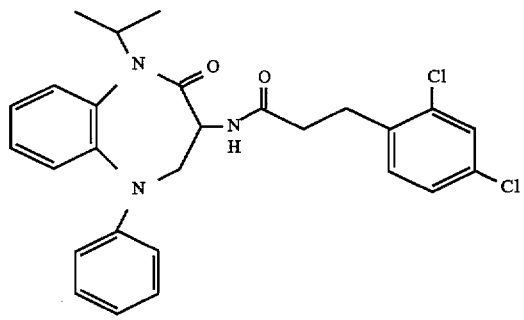

N-(4-Oxo-1-phenyl-5-(2-propyl)-2,3,4,5-tetrahydro-1H-1, 5-benzodiazepin-3-yl)-2-(3,5-dichlorophenyl) acetamide

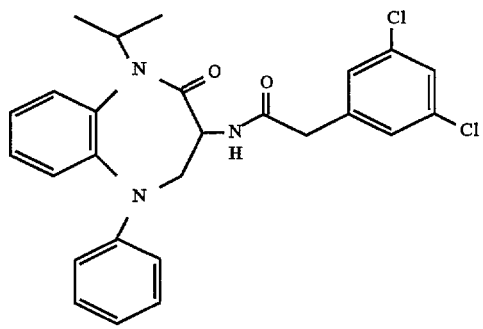

N-(4-Oxo-1-phenyl-5-(2-propyl)-2,3,4,5-tetrahydro-1H-1, 5-benzodiazepin-3-yl)-2-(2,4-dichlorophenyl) acetamide

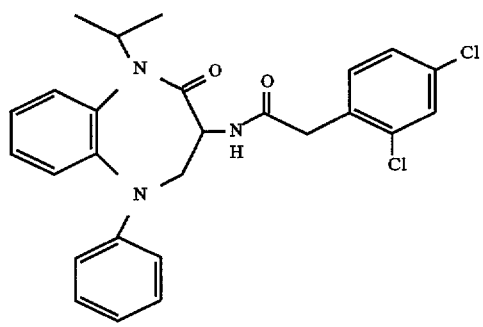

N-(4-Oxo-1-phenyl-5-(2-propyl)-2,3,4,5-tetrahydro-1H-1, 5-benzodiazepin-3-yl)-2-(2,4-bis(trifluoromethyl)phenyl) acetamide

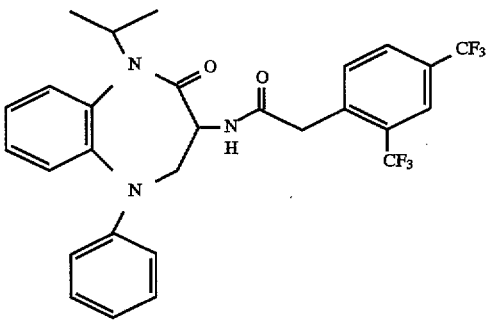

(RS)-N-(4-Oxo-1-phenyl-5-trifluoroethyl-2,3,4,5-tetrahydro-1H-1,5-benzodiazepin-3-yl)-2-(2,4-dichlorophenyl) acetamide

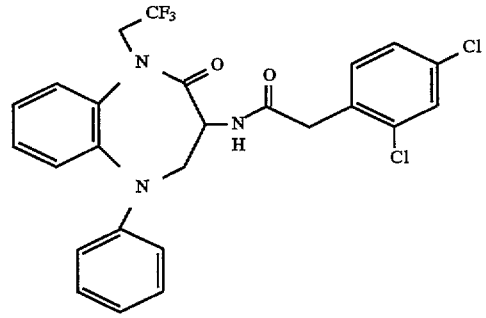

(−)-N-(1-Phenyl-4-oxo-5-(2-propyl)-2,3,4,5-tetrahydro-1H-1,5-benzodiazepin-3-yl)-2-(3,5-dichlorophenyl) acetamide

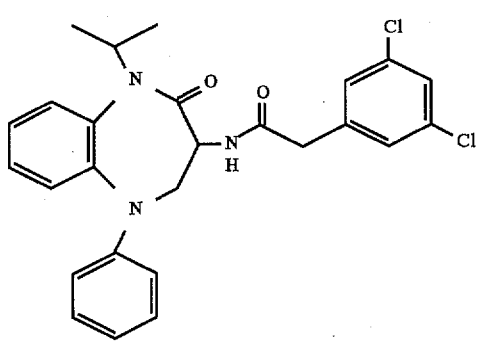

(−)-N-(1-Phenyl-4-oxo-5-(2-propyl)-2,3,4,5-tetrahydro-1H-1,5-benzodiazepin-3-yl)-2-(2,4-dichlorophenyl)acetamide

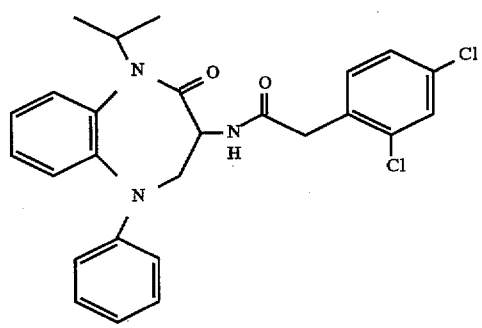

(−)-N-(1-Phenyl-4-oxo-5-(2-propyl)-2,3,4,5-tetrahydro-1H-1,5-benzodiazepin-3-yl)-2-(2,4-bis(trifluoromethyl)phenyl)acetamide

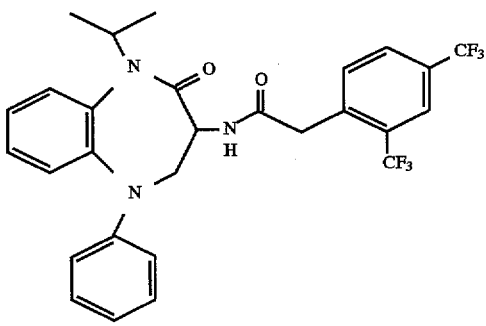

(+)-N-(1-Phenyl-4-oxo-5-(2-propyl)-2,3,4,5-tetrahydro-1H-1,5-benzodiazepin-3-yl)-2-(3,5-dichlorophenyl)acetamide.

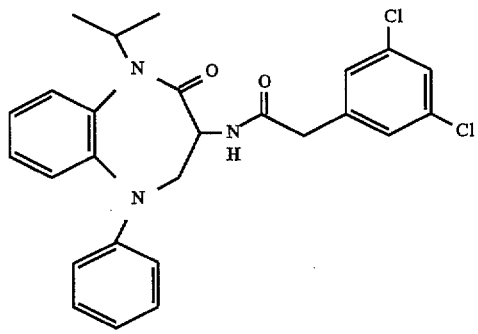

(+)-N-(1-Phenyl-4-oxo-5-(2-propyl)-2,3,4,5-tetrahydro-1H-1,5-benzodiazepin-3-yl)-2-(2,4-dichlorophenyl)acetamide.

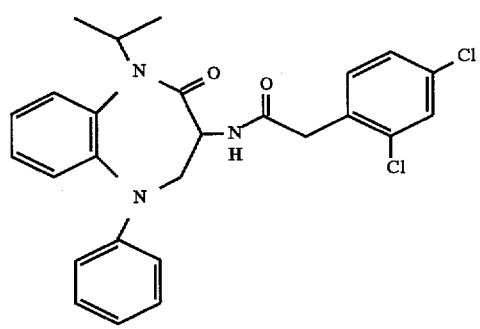

(+)-N-(1-Phenyl-4-oxo-5-(2-propyl)-2,3,4,5-tetrahydro-1H-1,5-benzodiazepin-3-yl)-2-(2,4-bis(trifluoromethyl)phenyl) acetamide

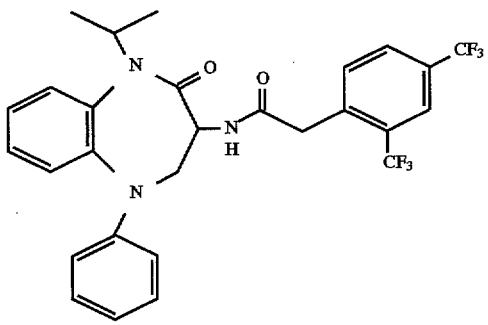

2-(2,4-Dichlorophenyl)-N-(1-isopropyl-5-phenyl-2,3,4,5-tetrahydro-1H-benzo[b][1,4]diazepin-3-yl)-acetamide

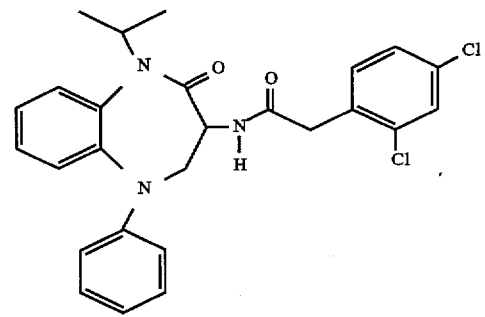

The novel processes for preparing the compounds of this invention are schematically exemplified below in the schemes. These steps are well known in the art and/or described in the Examples that follow.
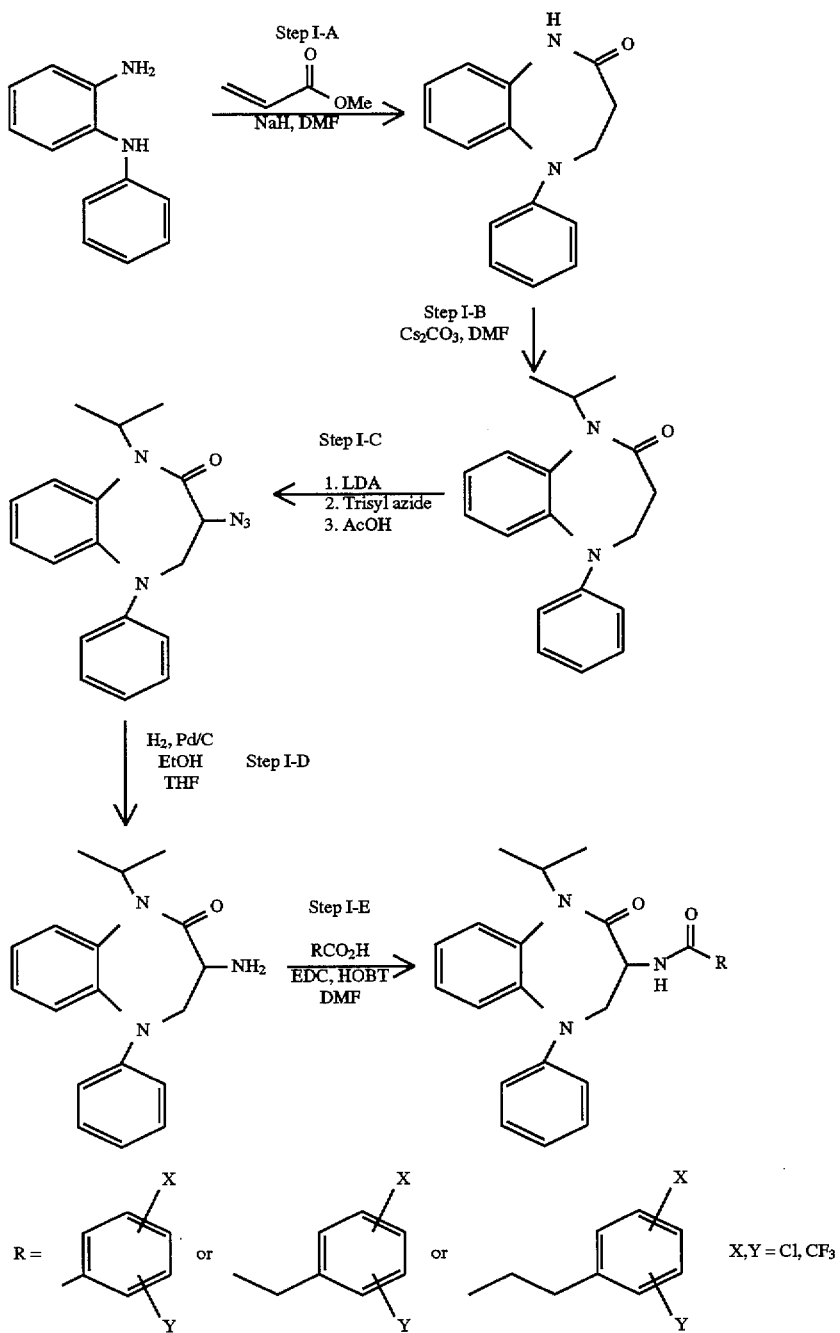
Scheme I

5,726,171
Scheme II
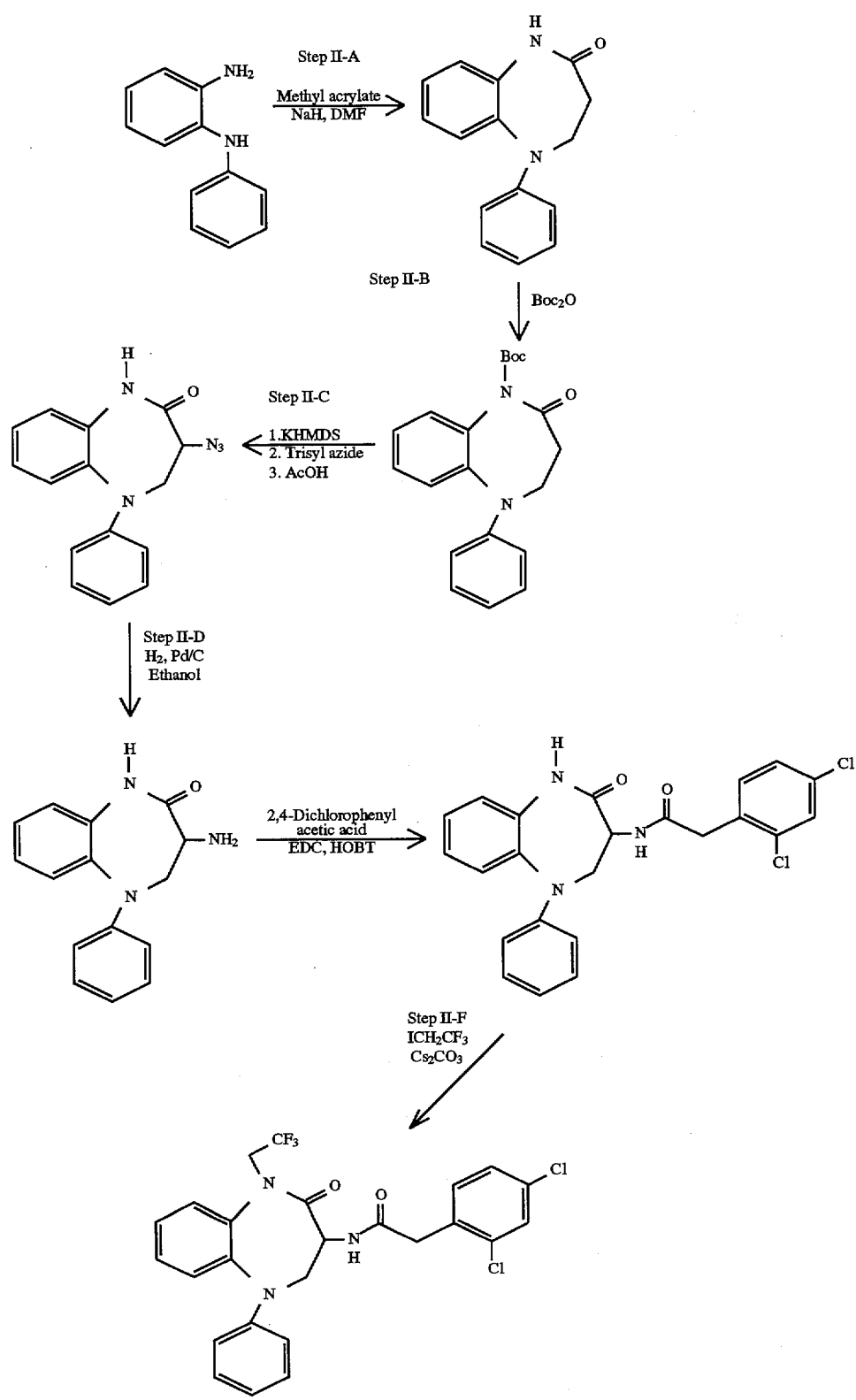

SCHEME III
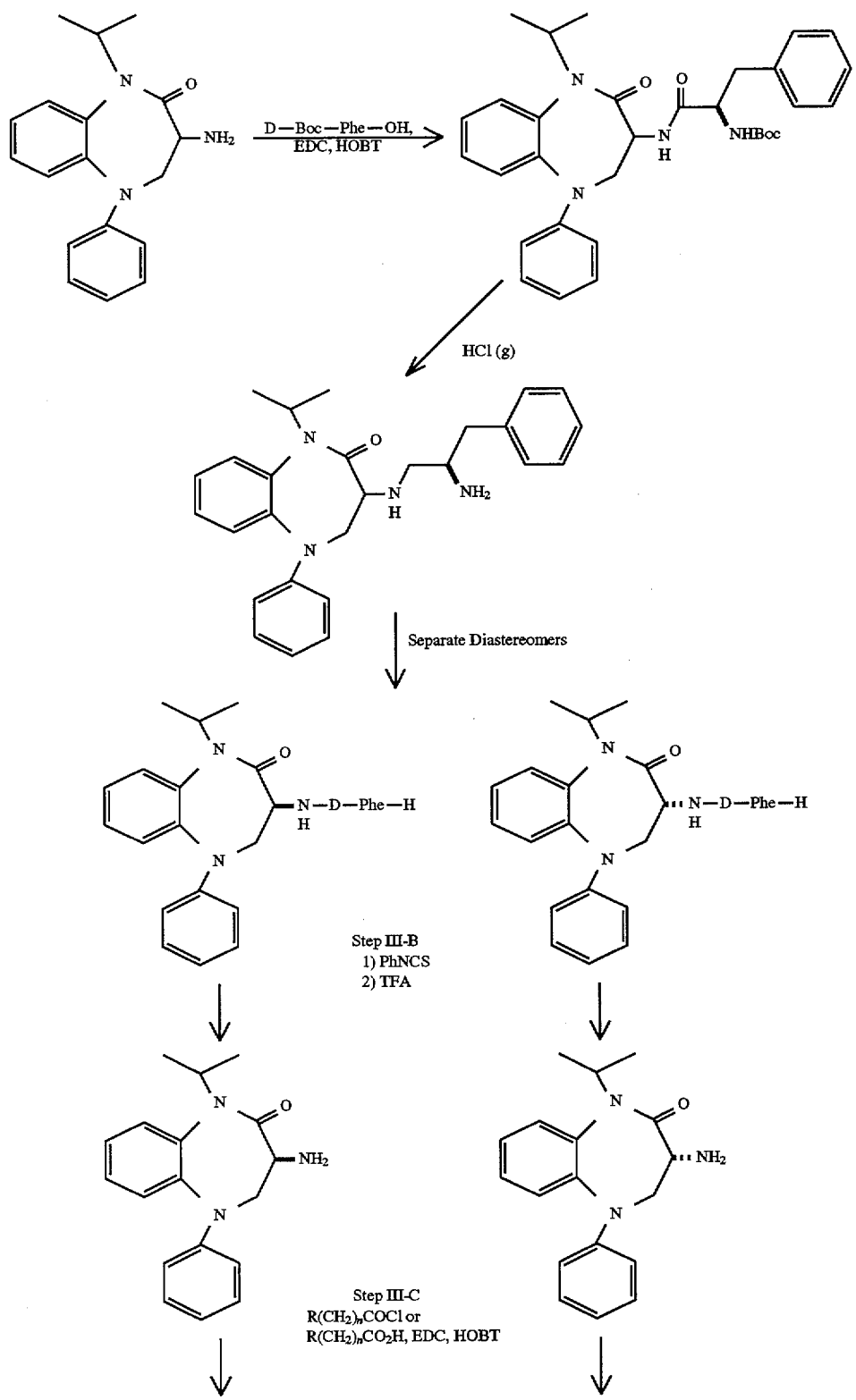

-continued
SCHEME III

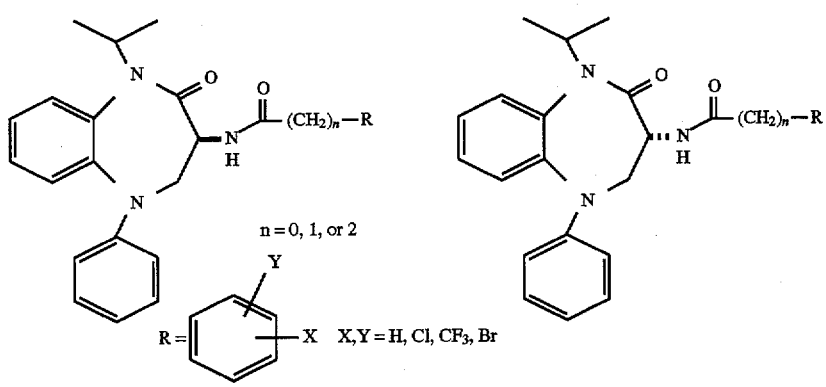

Scheme IV

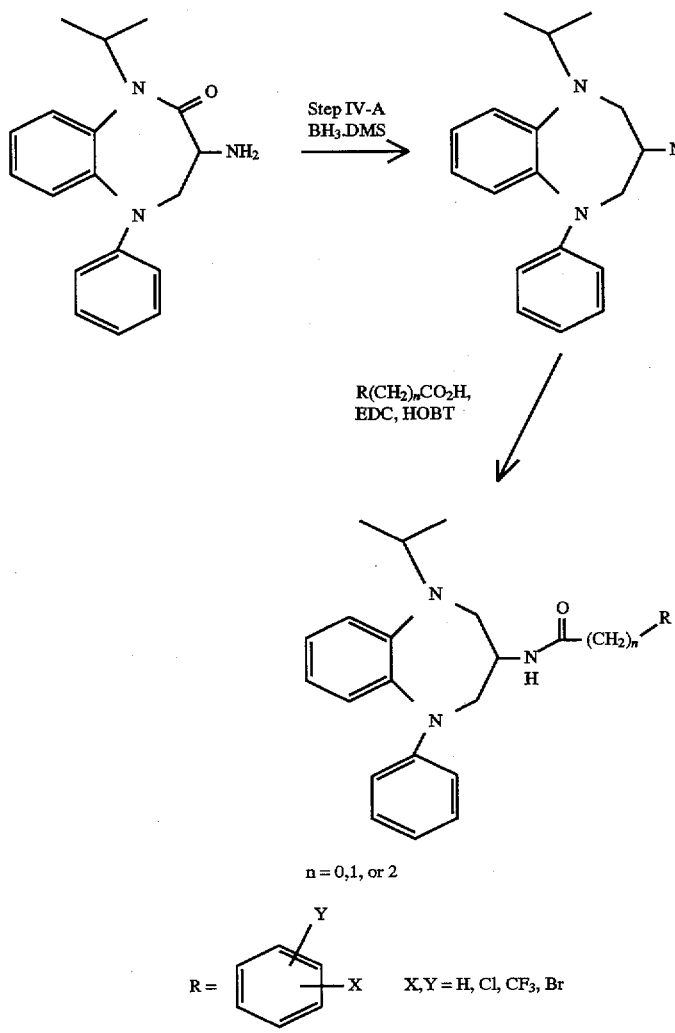

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 5.0 mg per kg of body weight per day in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrat. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as antiarrhythmic agents is measured by their ability to block the IKs and IKr currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K$^+$ current: differential sensitivity to block by Class III antiarrhythmic agents. J. Gen Physiol. 96: 195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4 KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). IKI is measured as peak outward current during the voltage ramp. IKr is measured as tail currents upon repolarization from −10 mV to −50 mV. IKs is measured as time-dependent current during the pulse to +50 mV. Currents are measured during control, then after exposure to drug at two different concentrations.

Employing this test the compounds described herein have an $IC_{50}$ of less than 1,000 nM as IKs blockers. The comounds of this invention are at least 10 times more potent in the blockade of IKs than the blockade of IKr.

EXAMPLES

In the following examples, reference is made to the steps outlined in the schemes found in the Detailed Description of the Invention. For example, Step 1-A refers to step A of Scheme 1.

Example 1

N-(4-Oxo-1-phenyl-5-(2-propyl)-2,3,4,5-tetrahydro-1H-1, 5-benzodiazepin-3-yl)-3-(2,4-dichlorophenyl) propionamide

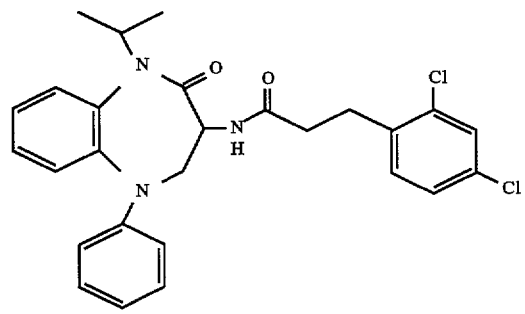

Step I-A: 1-Phenyl-1,5-benzodiazepin-4-one

A solution of N-phenyl-phenylenediamine (10 g, 54.3 mmole) in N,N-dimethylformamide (150 mL) at 0° C. was treated with sodium hydride (2.2 g of 60% dispersion in mineral oil, 54.3 mmole).

A solution of methyl acrylate (5.01 g, 59 mmole) in tetrahydrofuran (50 mL) was then added over 20 minutes. The reaction was warmed to ambient temperature and stirred for 2 hours. The reaction was poured into water (500 mL) and extracted with ethyl acetate (3×200 mL). The organic layers were combined, dried over anhydrous magnesium sulfate, filtered, and concentrated in vacuo. The residue was chromatographed on silica gel eluting with 1:1 ethyl acetate-:hexane to give 6.7 g of the product. mp. 176°–178° C. $^1$H NMR (300 MHz, CDCl$_3$) δ8.4 (br s, 1H), 7.30–7.00 (m, 6H), 6.90–6.70 (m, 3H), 4.05 (t, J=7 Hz, 2H), 2.65 (t, J=7 Hz, 2H).

Step I-B: 1-Phenyl-5-(2-propyl)-1,5-benzodiazepin-4-one

A solution of 1-phenyl-1,5-benzodiazepine-4-one (16.5 g, 0.069 mole) in N,N-dimethylformamide (80 mL) was treated with cesium carbonate (27.07 g, 0.083 mole) and 2-iodopropane (14.1 g, 0.083 mole). The reaction was stirred at room temperature for 24 hours. The mixture was diluted with ethyl acetate (300 mL) and poured into water (1 L). The organic layer was separated and the aqueous layer was extracted again with ethyl acetate (2×300 mL). The organic layers were combined, dried over anhydrous magnesium sulfate, filtered and concentrated in vacuo to give 14 g of product. mp. 138°–139° C. $^1$H NMR (300 MHz, CDCl$_3$) δ7.35–7.30 (m, 1H), 7.30–7.15 (m, 4H), 6.90–6.75 (m, 3H), 4.83 (sep, J=7 Hz, 1H), 4.10–3.90 (m, 1H), 3.80–3.60 (m, 1H), 2.65–2.40 (m, 2H), 1.42 (d, J=7 Hz, 3H), 1.07 (d, J=7 Hz, 3H).

Step I-C: 3-Azido-1-phenyl-5-(2-propyl)-1,5-benzodiazepin-4-one

To a stirring solution of diisopropylamine (6.1 mL, 0.046 mole) in tetrahydrofuran (50 mL), which was cooled to −78° C. in a dry ice/acetone bath, was added dropwise n-butyllithium (2.5M in hexanes, 18.5 mL). After ten minutes, a solution of 1-phenyl-5-(2-propyl)-1,5-benzodiazepin-4-one (10.0 g, 0.036 mole) in tetrahydrofuran (50 mL) was added dropwise. After ten minutes, 2,4,6-triisopropylbenzenesulfonyl azide (14.3 g, 0.046 mole) in tetrahydrofuran (40 mL) was added dropwise. After ten minutes, acetic acid (8.2 mL, 0.046 mole) in tetrahydrofuran (10 mL) was added in one portion and the reaction was warmed to room temperature over 12 hours. The reaction was poured into a solution of saturated sodium hydrogen carbonate (500 mL) and extracted with ethyl acetate (3×350 mL). The organic layers were combined, dried over anhydrous magnesium sulfate, filtered, and concentrated in vacuo. The residue was chromatographed on silica gel eluting with 1:9 ethyl acetate:hexane to give 8.6 g of product as a white solid (75%). $^1$H NMR (300 MHz, CDCl$_3$) δ7.37–7.06 (m, 6H), 6.89 (app t, J=7.3 Hz, 1H), 6.77 (d, J=7.8 Hz, 2H), 4.83 (sep, J=6.9 Hz, 1H), 3.94–3.80 (m, 3H), 1.43 (d, J=6.8 Hz, 3H), 1.15 (d, J=7.0 Hz, 3H).

Step I-D: 3-Amino-1-phenyl-5-(2-propyl)-1,5-benzodiazepin-4-one

A suspension of 10% palladium on carbon (1.0 g) in ethanol (150 mL) and 3-azido-1-phenyl-5-(2-propyl)-1,5-benzodiazepin-4-one (8.6 g, 0.029 mole) was stirred under hydrogen (1 atm) for 3 hours. The mixture was filtered through Celite and concentrated in vacuo. The residue was chromatographed on silica gel eluting with 97:3 ethyl acetate:methanol to give 7.2 g of the product as an amorphous solid (91%). $^1$H NMR (300 MHz, CDCl$_3$) d 7.37–7.05 (m, 6H), 6.85 (app t, J=7.3 Hz, 1H), 6.75 (d, J=7.8 Hz, 2H), 4.84 (sep, J=6.9 Hz, 1H), 3.82–3.70 (m, 1H), 3.59–3.42 (m, 2H), 1.44 (d, J=6.8 Hz, 3H), 1.12 (d, J=7.0 Hz, 3H).

Step I-E: N-(4-Oxo-1-phenyl-5-(2-propyl)-2,3,4,5-tetrahydro-1H-1,5-benzodiazepin-3-yl)-3-(2,4-dichlorophenyl) propionamide To a stirring solution of 3-amino-1-phenyl-5-(2-propyl)-1,5-benzodiazepin-4-one (120 mg, 0.41 mmole) in N,N-dimethylformamide (2 mL) was added EDC (93 mg, 0.49 mmole), HOBT (33 mg, 0.24 mmole) and 2,4-dichlorophenylpropionic acid (107 mg, 0.49 mmole). This was stirred at room temperature for 2 hours. The reaction was diluted with ethyl acetate (150 mL), then washed with 10% aqueous potassium hydrogen sulfate (75 mL) then saturated aqueous sodium hydrogen carbonate (75 mL) and finally, brine (50 mL). The organic layers were combined, dried over anhydrous magnesium sulfate, filtered, and concentrated in vacuo. The residue was chromatographed on silica gel eluting with 1:3 ethyl acetate:hexane to give 180 mg of product (89%), which was crystallized from ethyl acetate/hexane to give colorless crystals (60 mg). m.p.= 138°–140° C. $^1$H NMR (300 MHz, CDCl$_3$) δ7.40–7.14 (m, 11H), 6.87 (app t, J=7.2 Hz, 1H), 6.70 (d, J=8.6 Hz, 2H), 6.57 (d, J=7.2 Hz, 1H), 4.78 (sep, J=7.0 Hz, 1H), 4.60 (app d t, J=11, 6.7 Hz, 1H), 3.98 (d d, J=9.5, 6.7 Hz, 1H), 3.33 (d d, J=11, 9.5 Hz, 1H), 3.03 (t, J=7.2 Hz, 2H), 2.54 (t, J=7.2 Hz, 2H), 1.45 (d, J=7.0 Hz, 2H), 1.13 (d, J=6.9 Hz, 2H). Anal. Calcd. for $C_{27}H_{27}N_3O_3Cl_2$: C: 65.33; H: 5.48; N: 8.46. Found: C: 65.04; H: 5.45; N: 8.38.

Example 2

N-(4-Oxo-1-phenyl-5-(2-propyl)-2,3,4,5-tetrahydro-1H-1,5-benzodiazepin-3-yl)-2-(3,5-dichlorophenyl) acetamide

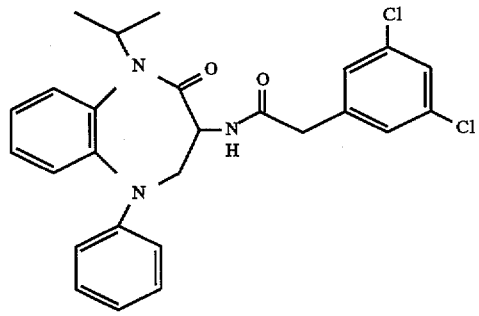

m.p.=170°–172° C. $^1$H NMR (300 MHz, CDCl$_3$) δ7.35–7.14 (m, 11H), 6.87 (app t, J=7.2 Hz, 1H), 6.80 (d, J=8.6 Hz, 2H), 6.68 (d, J=7.2 Hz, 1H), 4.78 (sep, J=7.0 Hz, 1H), 4.60 (app d t, J=11, 6.7 Hz, 1H), 3.98 (d d, J=9.5, 6.7 Hz, 1H), 3.53–3.43 (m, 3H), 1.45 (d, J=7.0 Hz, 2H), 1.13 (d, J=6.9 Hz, 2H). Anal. Calcd. for $C_{26}H_{25}N_3O_3Cl_2 \cdot 0.10$ hexane: C: 65.07; H: 5.42; N: 8.56. Found: C: 65.18; H: 5.35; N: 8.51.

Example 3

N-(4-Oxo-1-phenyl-5-(2-propyl)-2,3,4,5-tetrahydro-1H-1,5-benzodiazepin-3-yl)-2-(2,4-dichlorophenyl) acetamide

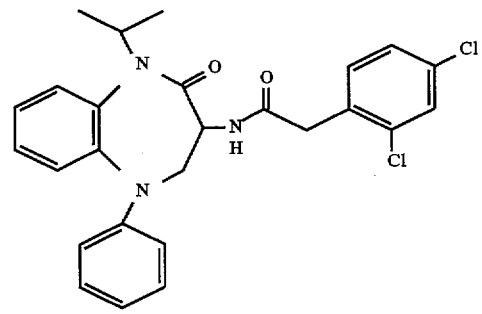

m.p.=215°–6° C. $^1$H NMR (300 MHz, CDCl$_3$) δ7.42 (s, 1H), 7.34–7.14 (m, 10H), 6.87 (app t, J=7.3 Hz, 1H), 6.78–6.67 (m, 3H), 4.79 (sep, J=7.0 Hz, 1H), 4.62 (app d t, J=10.5, 6.8 Hz, 1H), 4.09 (d d, J=9.6, 6.8 Hz, 1H), 3.68 (s, 2H), 3.46 (d d, J=10.5, 9.6 Hz, 1H), 1.44 (d, J=7.0 Hz, 2H), 1.11 (d, J=7.0 Hz, 2H). Anal. Calcd. for $C_{26}H_{25}N_3O_3Cl_2$: C: 64.73; H: 5.22; N: 8.71. Found: C: 64.37; H: 5.20; N: 8.67.

Example 4

N-(4-Oxo-1-phenyl-5-(2-propyl)-2,3,4,5-tetrahydro-1H-1,5-benzodiazepin-3-yl)-2-(2,4-bis(trifluoromethyl)phenyl) acetamide

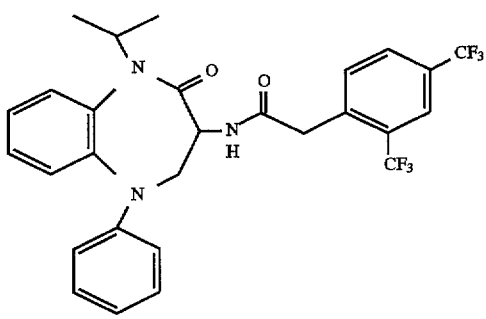

m.p.=123°–5° C. ¹H NMR (300 MHz, CDCl₃) δ7.92 (s, 1H), 7.78 (d, J=8.0 Hz, 1H), 7.61 (d, J=8.0 Hz, 1H), 7.34–7.13 (m, 8H), 6.87 (app t, J=7.2 Hz, 1H), 6.78 (d, J=6.8 Hz, 1H), 6.71 (d, J=12.5 Hz, 2H), 4.79 (sep, J=7.0 Hz, 1H), 4.62 (app d t, J=10.5, 6.8 Hz, 1H), 4.02–4.17 (m, 2H), 3.80 (s, 2H), 3.47 (d d, J=10.5, 9.6 Hz, 1H), 1.44 (d, J=7.1 Hz, 2H), 1.12 (d, J=7.0 Hz, 2H). Anal. Calcd. for C₂₆H₂₅N₃O₃Cl₂.0.10 hexane.0.40 EtOAc: C: 61.13; H: 5.03; N: 7.08. Found: C: 64.37; H: 5.20; N: 8.67.

Example 5

(RS)-N-(4-Oxo-1-phenyl-5-trifluoroethyl-2,3,4,5-tetrahydro-1H-1,5-benzodiazepin-3-yl)-2-(2,4-dichlorophenyl) acetamide

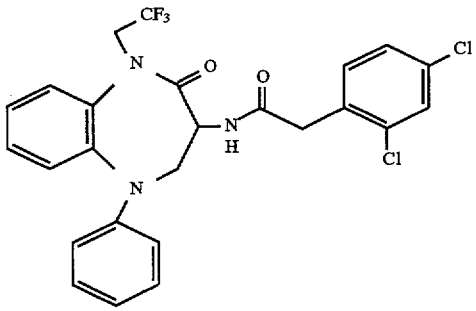

Step II-A: 5-Phenyl-1,5-benzodiazepine-2,-one.

A solution of N-phenyl-phenylenediamine (10 g, 54.3 mmole) in N,N-dimethylformamide (150 mL) at 0° C. was treated with sodium hydride (2.2 g of 60% dispersion in mineral oil, 54.3 mmole). A solution of methyl acrylate (5.01 g, 59 mmole) in tetrahydrofuran (50 mL) was then added over 20 minutes. The reaction was warmed to ambient temperature and stirred for 2 hours. The reaction was poured into water (500 mL) and extracted with ethyl acetate (3×200 mL). The organic layers were combined, dried over anhydrous magnesium sulfate, filtered, and concentrated in vacuo. The residue was chromatographed on silica gel eluting with 1:1 ethyl acetate:hexane to give 6.7 g of the product. mp. 176°–178° C. ¹H NMR (300 MHz, CDCl₃) δ8.4 (br s. 1H), 7.30–7.00 (m, 6H), 6.90–6.70 (m, 3H), 4.05 (t, J=7 Hz, 2H), 2.65 (t, J=7 Hz, 2H).

Step II-B: 1-(tert-butoxycarbonyl)-5-Phenyl-1,5-benzodiazepin-2-one

A solution of 1-phenyl-1,5-benzodiazepine-4-one (1.2 g, 5.0 mmole) in N,N-dimethylformamide (12 mL) was treated with di-tert-butyldicarbonate (1.10 g, 5.0 mmol), triethylamine (0.50 g, 5.0 mmol) and dimethylaminopyridine (0.18 g, 1.5 mmol). This was stirred at rt.. for 1 h. The reaction was then diluted with 200 mL water and extracted with ethyl acetate (2×100 mL). The organic phases were combined, dried with brine and sodium sulfate. This was evaporated under reduced pressure and the residue chromatographed over silica eluting with 20% ethyl acetate/hexane. The pure fractions were collected, evaporated under reduced pressure and evaporated again from ethyl ether to give 1.44 g, 86% of a white powder. ¹H NMR (300 MHz, CDCl₃) δ7.28–7.17 (m,6H), 6.88 (t,J=7.8 Hz, 1H), 6.80 (d,J=8.3 Hz,2H), 3.87 (t,J=6.6 Hz,2H), 2.59 (t,J=6.6 Hz,2H), 1.47 (s,9H)

Step II-C: 3-Azido-4-one-1-phenyl-1,5-benzodiazepine

To a solution of 1-(tert-butoxycarbonyl)-5-phenyl-1,5-benzodiazepin-2-one (1.45 g, 4.3 mmol) in tetrahydrofuran (15 mL) cooled to −78° C. was added a 0.5M solution of potassium bis[trimethylsilyl] amide in toluene (10.4 mL) dropwise. This was stirred for 5 min. and the triisopropylsulfonyl azide (1.6 g, 5.2 mmol) was added in tetrahydrofuran (3 mL). Acetic acid (0.31 g, 5.2 mmol) was then added and the reaction warmed to rt. The reaction was then diluted with saturated aqueous sodium bicarbonate (150 mL) and extracted with ethyl acetate (2×100 mL). The organic layers were combined, dried with brine and sodium sulfate. This was evaporated under reduced pressure. The residue was taken up in ethyl acetate (50 mL) and hydrogen chloride gas was bubbled through the solution while cooling in ice for 1 h. The reaction was diluted with saturated sodium bicarbonate (300 mL) and 50% sodium hydroxide (5 mL). Extracted with ethyl acetate (2×200 mL), combined organics, dried with brine, sodium sulfate and evaporated under reduced pressure. The residue was chromatographed over silica, eluting with 20% ethyl acetate/hexanes. The pure fractions were collected and evaporated under reduced pressure to give 0.8 g, 66.6% of a pale beige foam. ¹H NMR (300 MHz, CDCl₃) δ8.00 (s, 1H), 7.26–7.14 (m,6H), 6.90 (t,J=7.6 Hz, 1H), 6.76 (d,J=8.1 Hz,2H), 4.26–4.13 (m,2H), 3.92 (dxd,J= 11.0 and 11.0,1H)

Step II-D: 3-Amino-4-one-1-phenyl-1,5-benzodiazepine

To a stirring suspension of 10% palladium on activated carbon (0.30 g) in ethanol (25 mL) was added 3-azido-4-one-1-phenyl-1,5-benzodiazepine (0.75 g). Hydrogen was bubbled through this mixture for 10 min. and then it was stirred under 1 atm. hydrogen for 3 h. The reaction was then filtered, the catalyst rinsed with ethanol (4×20 mL) and evaporated under reduced pressure to give 0.34 g of a yellow glass which was carried forward without purification.

Step II-E: N-(4-Oxo-1-phenyl-2,3,4,5-tetrahydro-1H-1,5-benzodiazepin-3-yl)-2-(2,4-dichlorophenyl) acetamide To a stirring solution of 3-Amino-4-one-1-phenyl-1,5-benzodiazepine in N,N-dimethylformamide (10 mL) was added 1-Ethyl-3-(3-dimethylaminopropyl)-carbodiimide hydrochloride (0.38 g, 1.95 mmol), 1-Hydroxybenzotriazole hydrate (87.8 mg, 0.65 mmol) and 2,4-Dichlorophenylacetic acid (0.27 g, 1.3 mmol). This was stirred at rt. for 2 h. The reaction was then diluted with saturated aqueous sodium bicarbonate (1×75 mL) and extracted with ethyl acetate (2×30 mL). The organic layers were combined and washed with 0.1M HCl (1×50 mL) The organic layers were dried with brine and sodium sulfate and evaporated under reduced pressure. The residue was crystallized from diethyl ether to give 0.31 g 54.1% of a light brown solid ¹H NMR (300 MHz, CDCl₃) δ8.28 (s, 1H), 7.39 (d,J=2.0 Hz, 1H), 7.27–7.07 (m,8H), 6.84–6.76 (m,2H), 6.67 (d,J=8.5 Hz, 1H), 4.79 (dxdxd,J=11.7, 6.5 and 6.1 Hz, 1H), 4.30 (dxd,J=9.5 and 6.5 Hz, 1H), 3.66 (s,2H), 3.58 (dxd,J=11.7 and 9.5 Hz, 1H)

Step II-F: N-(4-Oxo-1-phenyl-5-trifluoroethyl-2,3,4,5-tetrahydro-1H-1,5-benzodiazepin-3-yl)- 2-(2,4-dichlorophenyl) acetamide To a stirring solution of N-(4-Oxo-1-phenyl-2,3,4,5-tetrahydro-1H-1,5-benzodiazepin-3-yl)-2-(2,4- dichlorophenyl) acetamide (0.3 g, 0.68 mmol) in N,N-Dimethylformamide (6.0 mL) was added cesium carbonate (0.44 g, 1.36 mmol) and 2,2,2-Trifluoroethyliodide (0.43 g,2.0 mmol). This was heated to 50° C. for 8 h. The reaction was then diluted with saturated aqueous sodium bicarbonate (1×50 mL) and extracted with ethyl acetate (2×20 mL). The organic layers were combined, washed with water (1×50 mL), dried with brine, sodium sulfate and evaporated under reduced pressure. The residue was chromatographed over silica, eluting with 20% ethyl acetate/hexane. The pure fractions were collected, evaporated under reduced pressure and the residue crystallized from ethyl ether to give 0.1g, 28.2% of a white powder. m.p. 205°–206° C. $^1$H NMR (300 MHz, CDCl$_3$) δ7.43 (s,1H), 7.24 (m,9H), 6.90 (t,J=8.1 Hz,1H), 6.74 (d,J=8.1Hz, 1H), 6.57 (d,J=7.1 Hz, 1H), 4.99 (dxq,J=15.3 and 8.3Hz, 1H), 4.80 (dxt,J=11.5 and 6.8 Hz, 1H), 4.19 (dxd,J=9.4 and 8.1 Hz, 1H), 4.05 (dxq,J=15.3 and 8.1 Hz, 1H), 3.68 (d,J=2.9 Hz,2H), 3.54 (dxd,J=11.2 and9.4 Hz, 1H). Anal. Calcd. for C$_{25}$H$_{20}$Cl$_2$F$_3$N$_3$O$_2$.0.05 Et2O: C, 57.54; H, 3.93; N, 7.99. Found: C, 57.9; H, 3.95; N, 7.99%.

Scheme III

The following examples were prepared by resolution of the amine product of Step I-D by a procedure depicted in scheme III followed by coupling with the appropriate carboxylic acids.

From the Stereo (−) amine was prepared the following three examples:

Example 6

(−)-N-(1-Phenyl-4-oxo-5-(2-propyl)-2,3,4,5-tetrahydro-1H-1,5-benzodiazepin-3-yl)-2-(3,5-dichlorophenyl) acetamide

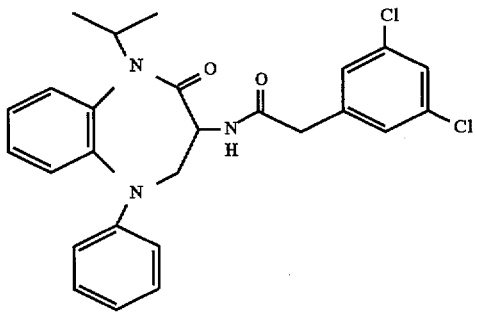

foam, [α]$_D$=−140° (c=0.45; MeOH). $^1$H NMR (300 MHz, CDCl$_3$) δ7.35–7.14 (m, 11H), 6.87 (app t, J=7.2 Hz, 1H), 6.80 (d, J=8.6 Hz, 2H), 6.68 (d, J=7.2 Hz, 1H), 4.78 (sep, J=7.0 Hz, 1H), 4.60 (app d t, J=11, 6.7 Hz, 1H), 3.98 (d d, J=9.5, 6.7 Hz, 1H), 3.53–3.43 (m, 3H), 1.45 (d, J=7.0 Hz, 2H), 1.13 (d, J=6.9 Hz, 2H). Anal. Calcd. for C$_{26}$H$_{25}$N$_3$O$_2$Cl$_2$. : C, 64.73; H, 5.22; N, 8.71. Found: C, 64.34; H, 5.35; N, 8.47%.

Example 7

(−)-N-(1-Phenyl-4-oxo-5-(2-propyl)-2,3,4,5-tetrahydro-1H-1,5-benzodiazepin-3-yl)-2-(2,4-dichlorophenyl) acetamide

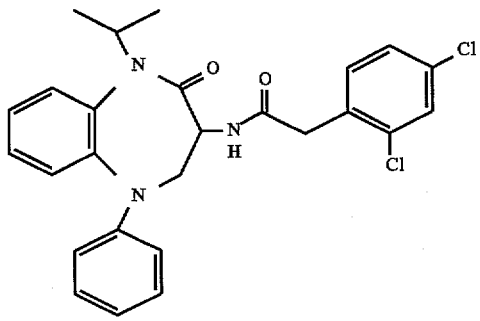

foam, [α]$_D$=−160° (c=0.64; MeOH). $^1$H NMR (300 MHz, CDCl$_3$) d 7.42 (s, 1H), 7.34–7.14 (m, 10H), 6.87 (app t, J=73 Hz, 1H), 6.78–6.67 (m, 3H), 4.79 (sep, J=7.0 Hz, 1H), 4.62 (app d t, J=10.5, 6.8 Hz, 1H), 4.09 (d d, J=9.6, 6.8 Hz, 1H), 3.68 (s, 2H), 3.46 (d d, J=10.5, 9.6 Hz, 1H), 1.44 (d, J=7.0 Hz, 2H), 1.11 (d, J=7.0 Hz, 2H). Anal. Calcd. for C$_{26}$H$_{25}$N$_3$O$_2$Cl$_2$.0.30 mol H$_2$O: C, 64.02; H, 5.29; N, 8.61. Found: C, 63.97; H, 5.29; N, 8.33%.

Example 8

(−)-N-(1-Phenyl-4-oxo-5-(2-propyl)-2,3,4,5-tetrahydro-1H-1,5-benzodiazepin-3-yl)-2-(2,4-bis(trifluoromethyl)phenyl)acetamide

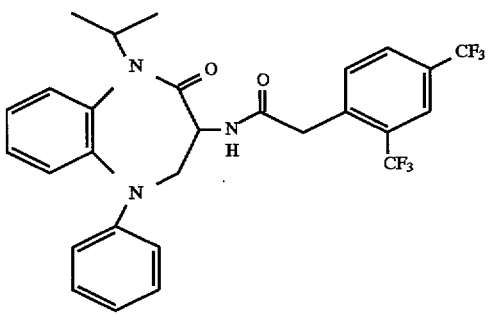

foam, [α]$_D$=−132° (c=0.46, MeOH). $^1$H NMR (300 MHz, CDCl$_3$) δ7.92 (s, 1H), 7.78 (d, J=8.0 Hz, 1H), 7.61 (d, J=8.0 Hz, 1H), 7.34–7.13 (m, 8H), 6.87 (app t, J=7.2 Hz, 1H), 6.78 (d, J=6.8 Hz, 1H), 6.71 (d, J=12.5 Hz, 2H), 4.79 (sep, J=7.0 Hz, 1H), 4.62 (app d t, J=10.5, 6.8 Hz, 1H), 4.02–4.17 (m, 2H), 3.80 (s, 2H), 3.47 (d d, J=10.5, 9.6 Hz, 1H), 1.44 (d, J=7.1 Hz, 2H), 1.12 (d, J=7.0 Hz, 2H). Anal. Calcd. for C$_{28}$H$_{25}$N$_3$O$_2$F$_6$: C, 61.2; H, 5.49; N, 7.65. Found: C, 60.85; H, 4.69; N, 7.53%.

From the stereo (+) amine was prepared the following three examples:

Example 9

(+)-N-(1-Phenyl-4-oxo-5-(2-propyl)-2,3,4,5-tetrahydro-1H-1,5-benzodiazepin-3-yl)-2-(3,5-dichlorophenyl) acetamide.

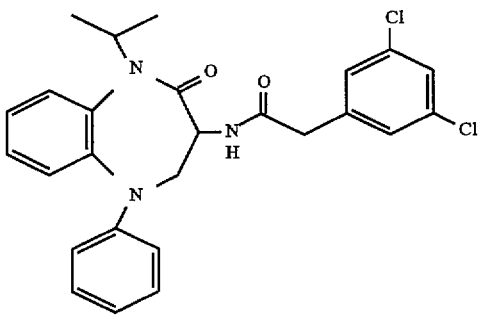

foam, [α]$_D$=+129° (c=0.34, MeOH). $^1$H NMR (300 MHz, CDCl$_3$) δ7.33–7.17 (m,8H), 6.87 (t,J=7.3 Hz, 1H), 6.74 (m,3H), 4.79 (h,J=6.8 Hz, 1H), 4.60 (ddd,J=6.6,6.7, and 11.3 Hz, 1H), 4.08 (dd,J=9.3 and 6.6 Hz, 1H), 3.50 (s,2H), 3.48 (dd,J=11.3 and 9.3 Hz, 1H), 1.45 (d,J=6.8 Hz,3H), 1.12 (d,J=6.8 Hz,3H) Anal. Calcd. for C$_{26}$H$_{25}$N$_3$O$_2$Cl$_2$. : C, 64.73; H, 5.22; N, 8.71. Found: C, 64.77; H, 5.39; N, 8.45%.

Example 10

(+)-N-(1-Phenyl-4-oxo-5-(2-propyl)-2,3,4,5-tetrahydro-1H-1,5-benzodiazepin-3-yl)-2-(2,4-dichlorophenyl) acetamide.

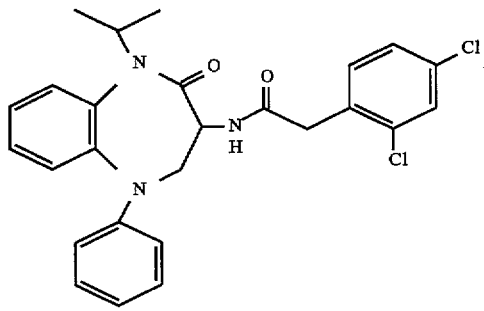

foam, [α]$_D$=+145° (c=0.37,MeOH). $^1$H NMR (300 MHz, CDCl$_3$) δ7.43 (d,J=2.0 Hz, 1H), 7.32–7.17 (m,7H), 6.86 (t,J=7.6 Hz, 1H), 6.72 (m,3H), 4.78 (h,J=6.8 Hz, 1H), 4.61 (ddd,J=6.6,6.6 and 11.2 Hz, 1H), 4.08 (dd,9.4 and 6.6 Hz, 1H), 3.67 (s,2H), 3.46 (dd,J=11.2 and 9.4 Hz, 1H), 1.43 (d,J=6.8 Hz,3H), 1.10 (d,J=6.8 Hz,3H) Anal. Calcd. for C$_{26}$H$_{25}$N$_3$O$_2$Cl$_2$.0.10 H2O 0.20 hexanes: C, 65.15; H, 5.63; N, 8.38. Found: C, 65.2; H, 5.59; N, 8.36%.

Example 11

(+)-N-(1-Phenyl-4-oxo-5-(2-propyl)-2,3,4,5-tetrahydro-1H-1,5-benzodiazepin-3-yl)-2-(2,4-bis(trifluoromethyl) phenyl) acetamide

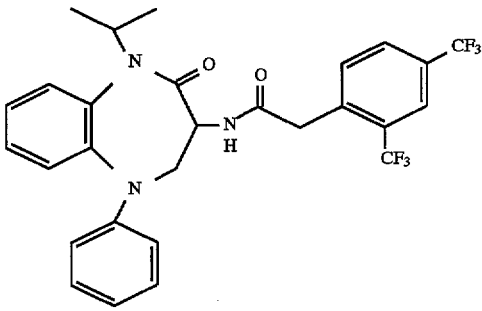

foam, [α]$_D$=+124° (c=0.47,MeOH). $^1$H NMR (300 MHz, CDCl$_3$) δ7.92 (s, 1H), 7.79 (d,J=7.8 Hz, 1H), 7.62 (d,J=8.3 Hz, 1H), 7.32–7.17 (m,5H), 6.86 (t,J=7.3 Hz, 1H), 6.74 (m,3H), 4.79 (h,J=6.8 Hz, 1H), 4.60 (ddd,J=6.8,6.6 and 11.2 Hz, 1H), 4.06 (dd,J=9.4 and 6.6 Hz, 1H), 3.81 (s,2H), 3.47 (dd,J=11.2 and 9.4 Hz, 1H), 1.44 (d,J=6.8 Hz,3H), 1.12 (d,J=6.8 Hz,3H) Anal. Calcd. for C$_{28}$H$_{25}$N$_3$O$_2$F$_6$.: C, 61.2; H, 4.59; N, 7.65. Found: C, 61.28; H, 4.72; N, 7.54%.

Example 12

2-(2,4-Dichlorophenyl)-N-(1-isopropyl-5-phenyl-2,3,4,5-tetrahydro-1H-benzo[b][1,4] diazepin-3-yl)-acetamide

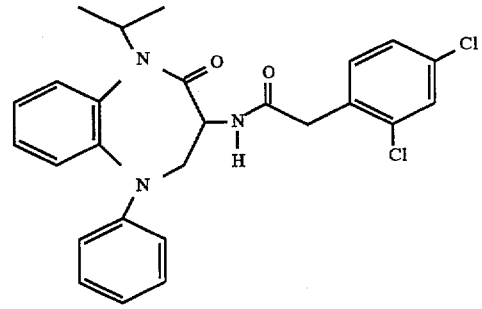

Step IV-A: 1-Isopropyl-5-phenyl-2,3,4,5-tetrahydro-1H-benzo[b][1,4] diazepin-3-yl amine To a stirring soultion of the product of step I-D above (3-Amino-1-phenyl-5-(2-propyl)-1,5-benzodiazepin-4-one) (1.4 mmol,0.4 g) in tetrahydrofuran (8 mL) was added BH$_3$•S(CH$_3$)$_2$ (1.8 eq,0.24 mL of a 10.1M solution). This was heated to reflux for 12 h. 1M hydrochloric acid (5 mL) was then added to the reaction and this was refluxed for 4 h. The reaction was then diluted with saturated sodium bicarbonate (100 mL) and extracted with ethyl acetate (2×50 mL). The organic layers were combined, dried with brine and sodium sulfate. This was evaporated under reduced pressure to a white powder which was carried forward without further purification.

Step IV-B: 2-(2,4-Dichlorophenyl)-N-(1-isopropyl-5-phenyl-2,3,4,5-tetrahydro-1H-benzo[b][1,4] diazepin-3-yl)-acetamide To a stirring solution of the above crude mixture in DMF (10 mL) was added 2,4-dichlorophenylacetic acid (1.4 mmol, 0.29 g), 1-ethyl-3-(3-dimethylaminopropyl) corbodiimide•HCl (2.1 mmol, 0.40 g), and 1-hydroxybenztriazole hydrate (0.7 mmol, 94.6 mg). This was stirred at rt for 2 h. The reaction was then diluted with 10% aqueous potassium hydrogen sulfate (100 mL) and extracted with ethyl acetate (2×50mL). The organic layers were combined, washed with saturated sodium bicarbonate (1×100 mL), water (1×100 mL), dried with brine and sodium sulfate and evaporated under reduced pressure. The resulting residue was chromatographed with 20% ethyl acetate:hexane. The major spot was collected and evaporated under reduced pressure to give 0.4 g of a white powder. m.p. 175°–177° C. $^1$H NMR (DMSO) δ8.06 (bs,1H), 7.55 (d,J= 1.7 Hz, 1H), 7.38–7.31 (m,2H), 7.15–6.91 (m,5H), 6.79–6.64 (m,4H), 4.11–3.97 (m,2H), 3.90–3.75 (m, 1H), 3.56 (s,2H), 3.55–3.45 (m, 1H), 3.05–2.85 (m,2H), 1.10 (d,J=6.3 Hz,3H), 0.96 (d,J=6.3 Hz,3H) Anal. Calcd. for $C_{26}H_{27}Cl_2N_3O \cdot 0.15\ H_2O$: C, 66.29; H, 5.84; N, 8.92. Found: C, 66.29; H, 5.8; N, 8.89%.

What is claimed is:

1. A compound of the structural formula I

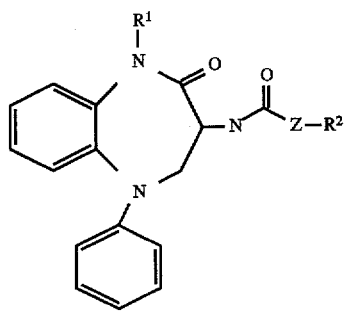

FORMULA I where $R^1$ is $C_{1-6}$ alkyl, either straight or branch chain; substituted $C_{1-6}$alkyl, either straight or branch chain wherein the substitutents are selected from F, $C_{3-8}$ cycloalkane, —OH, —CF$_3$;

and

Z is

1) $C_{1-6}$ alkyl, either straight or branched chain, 2) substituted $C_{1-6}$ alkyl, either straight or branched chain, wherein the substitutents are selected from F, NO$_2$, OH, 2) $C_{2-4}$ alkenylene, either straight or branch chain, 3) —(CH$_2$)$_m$—W—(CH$_2$)$_n$— wherein m and n are independently 0, 1, 2, 3 or 4 and W is —O—, —S— or —NH, 4) $C_{3-6}$ cycloalkane, 5) $C_{3-6}$ cycloalkylene, or 6) single bond;

$R^2$ is 1) phenyl, either unsubstituted or substituted with one or two substituents selected from
   a) —NO$_2$, —OH,
   b) —Cl, Br, F, or I,
   c) —CF$_3$,
   d) —C$_{1-3}$ alkyl,
   e) —C$_{1-3}$ alkoxy,
   f) —CN,
   g) -methylenedioxy, 2) $C_{5-7}$ cycloalkyl, either unsubstituted or substituted with one or two substitutents selected from
   a) —NO$_2$, OH,
   b) —F,
   c) —CF$_3$,
   d) —C$_{1-3}$ alkyl,
   e) —C$_{1-3}$ alkoxy,
   f) —CN,
   g) -methylenedioxy, as the racemates, mixtures of enantiomers, individual diastereomers or individual enantiomers, and pharmaceutically acceptable crystal forms, salts, or hydrates thereof.

2. The compound of claim 1 selected from N-(4-Oxo-1-phenyl-5-(2-propyl)-2,3,4,5-tetrahydro-1H-1,5-benzodiazepin-3-yl)-3-(2,4-dichlorophenyl) propionamide

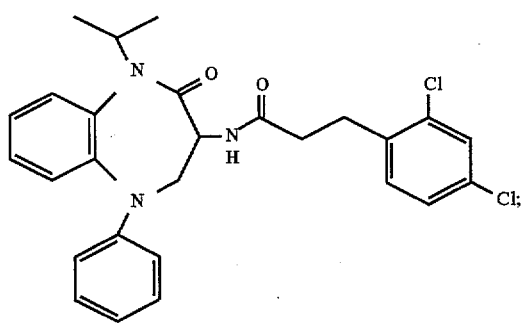

N-(4-Oxo-1-phenyl-5-(2-propyl)-2,3,4,5-tetrahydro-1H-1,5-benzodiazepin-3-yl)-2-(3,5-dichlorophenyl) acetamide N-(4-Oxo-1-phenyl-5-(2-propyl)-2,3,4,5-tetrahydro-1H-1,5-benzodiazepin-3-yl)-2-(2,4-dichlorophenyl) acetamide N-(4-Oxo-1-phenyl-5-(2-propyl)-2,3,4,5-tetrahydro-1H-1,5-benzodiazepin-3-yl)-2-(2,4-bis(trifluoromethyl)phenyl) acetamide (RS)-N-(4-Oxo-1-phenyl-5-trifluoroethyl-2,3,4,5-tetrahydro-1H-1,5-benzodiazepin-3-yl)-2-(2,4-dichlorophenyl) acetamide

27

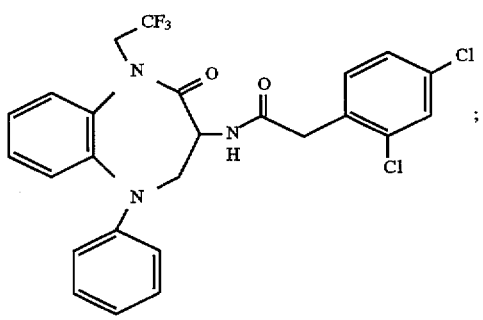

(−)-N-(1-Phenyl-4-oxo-5-(2-propyl)-2,3,4,5-tetrahydro-1H-1,5-benzodiazepin-3-yl)-2-(3,5-dichlorophenyl) acetamide

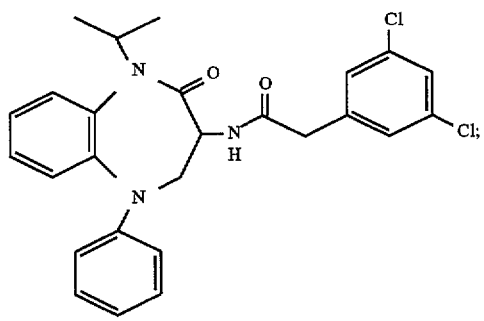

(−)-N-(1-Phenyl-4-oxo-5-(2-propyl)-2,3,4,5-benzodiazepin-3-yl)-2-(2,4-dichlorophenyl) acetamide

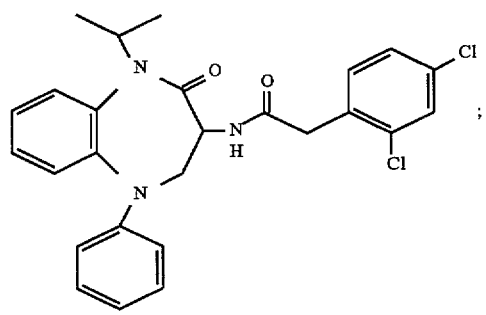

(−)-N-(1-Phenyl-4-oxo-5-(2-propyl)-2,3,4,5-tetrahydro-1H-1,5-benzodiazepin-3-yl)-2-(2,4-bis(trifluoromethyl) phenyl)acetamide

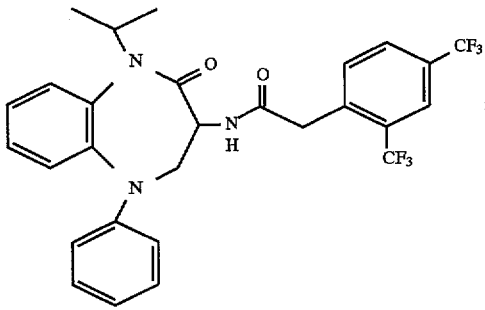

(+)-N-(1-Phenyl-4-oxo-5-(2-propyl)-2,3,4,5-tetrahydro-1H-1,5-benzodiazepin-3-yl)-2-(3,5-dichlorophenyl) acetamide.

28

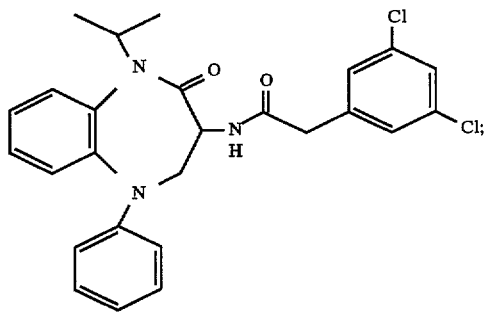

(+)-N-(1-Phenyl-4-oxo-5-(2-propyl)-2,3,4,5-tetrahydro-1H-1,5-benzodiazepin-3-yl)-2-(2,4-dichlorophenyl) acetamide.

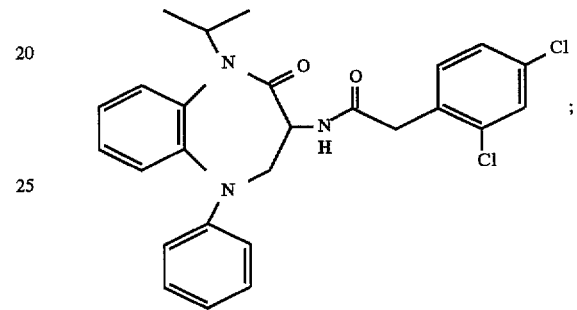

(+)-N-(1-Phenyl-4-oxo-5-(2-propyl)-2,3,4,5-tetrahydro-1H-1,5-benzodiazepin-3-yl)-2-(2,4-bis(trifluoromethyl) phenyl) acetamide

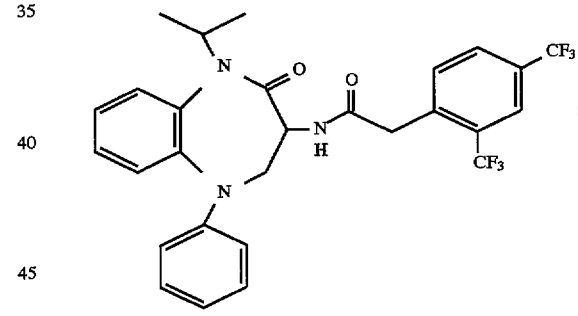

or
2-(2,4-Dichlorophenyl)-N-(1-isopropyl-5-phenyl-2,3,4,5-tetrahydro-1H-benzo[b][1,4] diazepin-3-yl)-acetamide

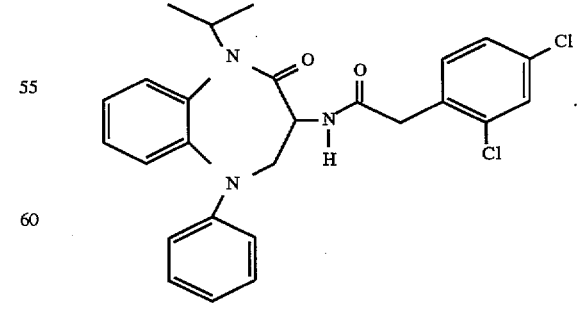

3. The compound of claim 1 which is N-(4-Oxo-1-phenyl-5-(2-propyl)-2,3,4,5-tetrahydro-1H-1,5-benzodiazepin-3-yl)-3-(2,4-dichlorophenyl) propionamide

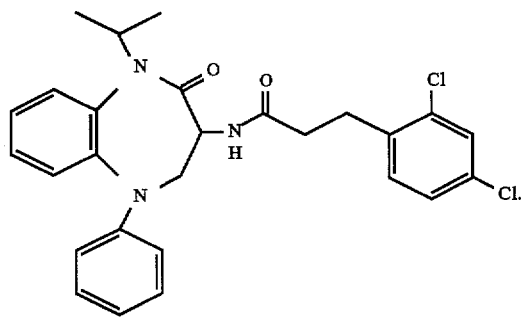

4. The compound of claim 1 which is N-(4-Oxo-1-phenyl-5-(2-propyl)-2,3,4,5-tetrahydro-1H-1,5-benzodiazepin-3-yl)-2-(3,5-dichlorophenyl) acetamide

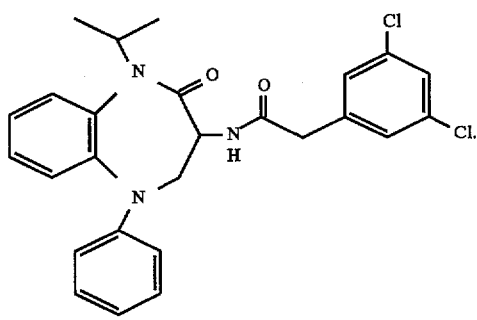

5. The compound of claim 1 which is N-(4-Oxo-1-phenyl-5-(2-propyl)-2,3,4,5-tetrahydro-1H-1,5-benzodiazepin-3-yl)-2-(2,4-dichlorophenyl) acetamide

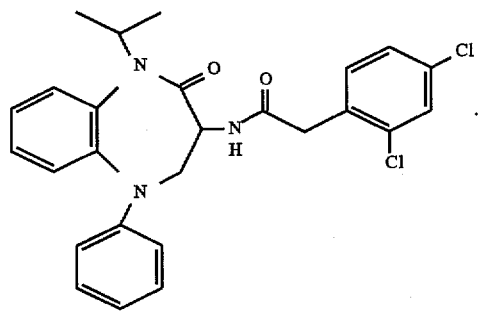

6. The compound of claim 1 which is N-(4-Oxo-1-phenyl-5-(2-propyl)-2,3,4,5-tetrahydro-1H-1,5-benzodiazepin-3-yl)-2-(2,4-bis(trifluoromethyl)phenyl) acetamide

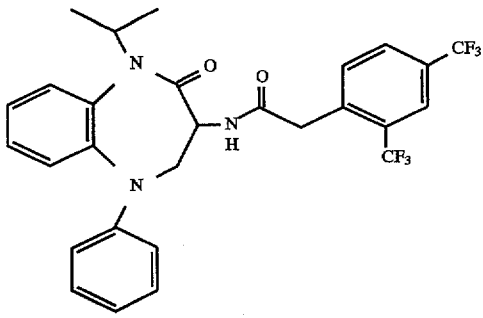

7. The compound of claim 1 which is (RS)-N-(4-Oxo-1-phenyl-5-trifluoroethyl-2,3,4,5-tetrahydro-1H-1,5-benzodiazepin-3-yl)-2-(2,4-dichlorophenyl) acetamide

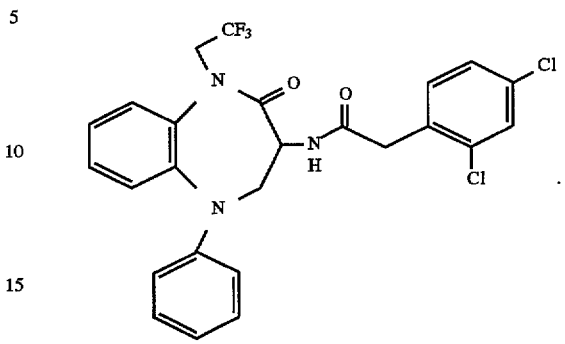

8. The compound of claim 1 which is (−)-N-(1-Phenyl-4-oxo-5-(2-propyl)-2,3,4,5-tetrahydro-1H-1,5-benzodiazepin-3-yl)-2-(3,5-dichlorophenyl) acetamide

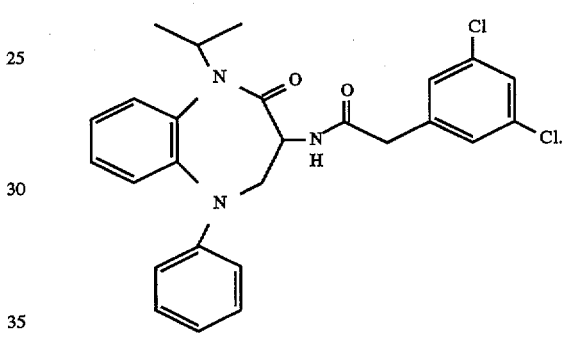

9. The compund of claim 1 whcih is (−)-N-(1-Phenyl-4-oxo-5-(2-propyl)-2,3,4,5-tetrahydro-1H-1,5-benzodiazepin-3-yl)-2-(2,4-dichlorophenyl)acetamide

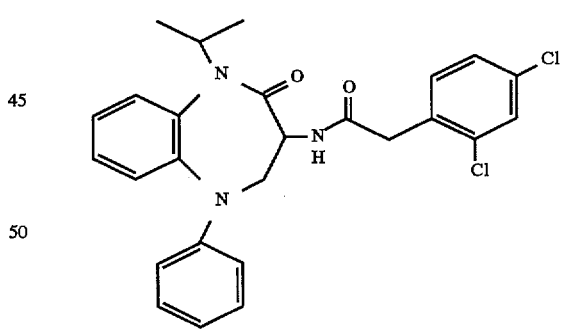

10. The compound of claim 1 which is (−)-N-(1-Phenyl-4-oxo-5-(2-propyl)-2,3,4,5-tetrahydro-1H-1,5-benzodiazepin-3-yl)-2-(2,4-bis(trifluoromethyl)phenyl) acetamide

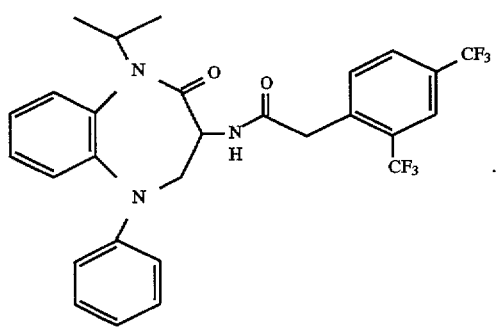

11. The compound of claim 1 which is (+)-N-(1-Phenyl-4-oxo-5-(2-propyl)-2,3,4,5-tetrahydro-1H-1,5-benzodiazepin-3-yl)-2-(3,5-dichlorophenyl) acetamid

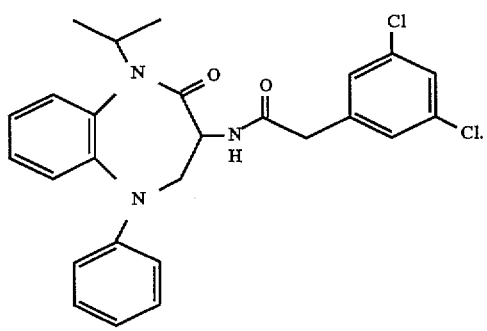

12. The compound of claim 1 which is (+)-N-(1-Phenyl-4-oxo-5-(2-propyl)-2,3,4,5-tetrahydro-1H-1,5-benzodiazepin-3-yl)-2-(2,4-dichlorophenyl) acetamide.

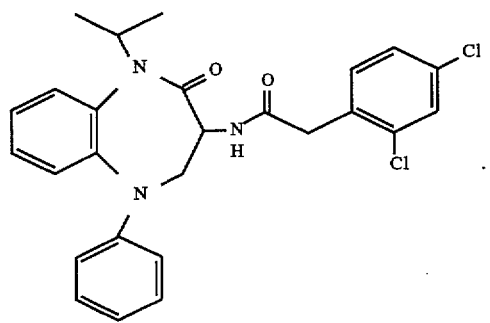

13. The compound of claim 1 which is (+)-N-(1-Phenyl-4-oxo-5-(2-propyl)-2,3,4,5-tetrahydro-1H-1,5-benzodiazepin-3-yl)-2-(2,4-bis(trifluoromethyl)phenyl) acetamide

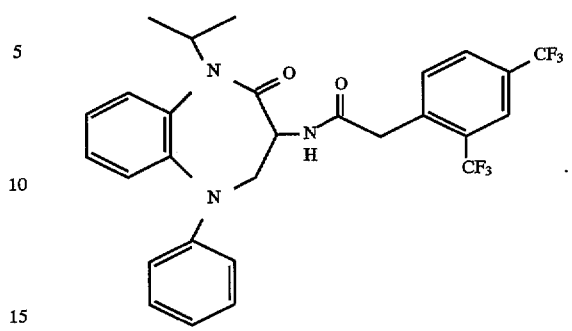

14. The compound of claim 1 which is 2-(2,4-Dichlorophenyl)-N-(1-isopropyl-5-phenyl-2,3,4,5-tetrahydro-1H-benzo[b][1,4] diazepin-3-yl)-acetamide

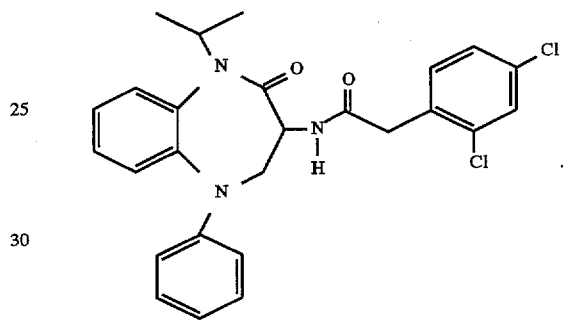

15. A pharmaceutical formulation comprising a pharmaceutically acceptable carrier and a therapeutically effective amount of the compound of claim 1 or a pharmaceutically acceptable salt, crystal form or hydrate thereof.

16. The pharmaceutical formulation of claim 15 comprising in addition another antiarrhythmic agent or other cardiovascular agent.

17. A method of preventing or treating arrhythmia which comprises the administration to a patient in need of such treatment of an antiarrhythmically effective amount of the compound of claim 1.

18. The method of claim 17 comprising the concomitant administration of another antiarrhithimic agent or other cardiovascular agent.

* * * * *

UNITED STATES PATENT AND TRADEMARK OFFICE
CERTIFICATE OF CORRECTION

PATENT NO. : 5,726,171
DATED : March 10, 1998
INVENTOR(S) : David A. Claremon, et al It is certified that error appears in the above-indentified patent and that said Letters Patent is hereby corrected as shown below:

On the title page, item [73] Assignee, insert the following:
-- Merck & Co., Inc., Rahway, New Jersey --

Signed and Sealed this

Twenty-first Day of July, 1998

Attest:

BRUCE LEHMAN

Attesting Officer

Commissioner of Patents and Trademarks